US007166569B2

(12) United States Patent
Fahy (10) Patent No.: US 7,166,569 B2
(45) Date of Patent: Jan. 23, 2007

(54) METHOD FOR THE PREVENTION OF TRANSPLANT REJECTION

(76) Inventor: Gregory M. Fahy, Box 2517, Gaithersburg, MD (US) 20886

( * ) Notice: Subject to any disclaimer, the term of this patent is extended or adjusted under 35 U.S.C. 154(b) by 792 days.

(21) Appl. No.: 09/933,309

(22) Filed: Aug. 20, 2001

(65) Prior Publication Data

US 2002/0016286 A1 Feb. 7, 2002

Related U.S. Application Data

(62) Division of application No. 08/251,384, filed on May 31, 1994, now Pat. No. 6,297,212.

(51) Int. Cl.
*A61K 38/00* (2006.01)
*C07K 14/00* (2006.01)
(52) U.S. Cl. ............................. 514/2; 530/399; 530/350
(58) Field of Classification Search ................. 514/2; 530/399; 424/93.1
See application file for complete search history.

(56) References Cited

OTHER PUBLICATIONS

"Insulin Resistance, A Multifaceted Syndrome Responsible for NIDDM, Obesity, Hypertension, Dyslipidemia, and Atherosclerotic Cardiovascular Disease,"Diabetes Care, vol. 14, No. 3, Mar. 1991, DeFronzo et al., pp. 173-194.
"Effects of One Year of Supplentation with Zinc and Other Micronutrients on Cellular Immunity in the Elderly,"Journal of the American College of Nutrition, vol. 9, No. 3, pp. 214-225 (1990), Bogden et al.
"Dietary Modulation of the Immune Response in the Aged,"Age, vol. 14, pp. 108-115, 1991, Meydani.
"Effects of Short Term Administration of Recombinant Human Growth Hormone to Elderly People, Journal of Clinical Endocrinology and Metabolism,"vol. 70, No. 2, pp. 519-527, Marcus et al., 1990.
"Exogenous Growth Hormone Treatment Alters Body Compositions and Increases Natural Killer Cell Activity in Women with Impaired Endogenous Growth Hormone Section,"Metabolism, vol. 36, No. 12 (Dec.), 1987, pp. 1115-1117 Crist et al.
"Growth Hormane treatment stimulates thymulin production in aged dogs", Clin. exp. Immunol., (1987) 68, pp. 580-587, Goff et al.
"$GH_3$ pituitary adenoma cells can reverse thymic aging in rats," Proc. Natl. Acad. Sci. USA, vol. 83, pp. 5663-5667, Aug. 1986, Kelley et al.

"Effects of Long-Term, Low-Dose Growth Hormone Therapy on Immune Function and Life Expectancy of Mice, Mechanisms of Ageing and Development," 57 (1991) pp. 87-100, Khansari et al.
"A Nonpeptidyl Growth Hormone Secretagogue," Science, vol. 260, Jun. 11, 1993, pp. 1640-1643, Smith et al.
"Effects of Human Growth Hormone in Men Over 60 Years Old," Journal of Medicine, vol. 323, Jul. 5, 1990, No. 1, pp. 1-6, Rudman et al.
"Effects of Human Growth Hormone on Body Composition in Elderly Men," Horm Res. 1991;36(suppl 1), pp. 73-81, Rudman et al.
"Evaluation of intrathymic islet transplantation in the prediabetic period, "Surgery Aug. 1992, pp. 319-326, Brayman et al.
"Lack of Effect of Dehydroepiandrosterone in Obese Men", International Journal of Obesity (1990), 14, pp. 457-463, Usiskin et al.
"Dehydroepiandrosterone: the "missing link" between hyperinsulinemia and atheroclerosis?,"The FASEB Journal, vol. 6, Sep. 1992, pp. 3073-3075, Nestler et al.
"The Effects of Oral Dehydroepiandrosterone on Endocrine-Metabolic Parameters in Postmenopausal Women,"Journal of Clinical Endocrinology and Metabolism, vol. 71, No. 3, pp. 696-704, Mortola et al.
"Bimodal Correlation between the Circulating Insulin Level and the Production Rate of Dehydroepiandrosterone: Positive Correlation in Controls and Negative Correlation in the Polycystic Ovary Syndrome with Acanthosis Nigricans," Journal of Clinical Endocrinology and Metabolism, vol. 70, 4, 1990, pp. 1075-1081, Farah et al.
"Dietary Chromium Supplementation with or without Somatotropin Treatment Alters Serum Hormones and Metabolites in Growing Pigs without Affecting Growth Performance," 1993 American Institute of Nutrition, pp. 1504-1512, Evock-Clover et al.
"Chromium Picolinate Increases Longevity," Evans et al., AGE, vol. 15, p. 134, Abstract 51, 1992.
"Hormone may restore muscle in elderly," Fackelmann, Science News, Jul. 14, 1990.
"New Transplant Method Evades Immune Attack," Naji, Science vol. 249, p. 1248, 1990.
"Induction of Donor-Specific Unresponsiveness by Intrathymic Islet Transplantation," Posselt et al., Science vol. 249, pp. 1293-1295, 1990.

(Continued)

*Primary Examiner*—Marianne P. Allen
*Assistant Examiner*—Regina M. DeBerry
(74) *Attorney, Agent, or Firm*—Price, Heneveld, Cooper, DeWitt & Litton, LLP (57) ABSTRACT

Human growth hormone therapy and thymic regeneration are effected by the generally simultaneous administration of one of human growth hormone, its analogs, precursors, metabolites, releasers or mixtures thereof in combination with one of DHEA, its precursors, releasers, analogs, metabolites or combinations thereof.

10 Claims, 2 Drawing Sheets

OTHER PUBLICATIONS

"Promotion of rat cardiac allograft survival by intrathymic inoculation of donor splenocytes," Odorico et al., Transplantation vol. 55, No. 5, pp. 1104-1107, May 1993.

"Kidney graft survival in rats without immunosuppressants after intrathymic glomerular transplantation," Remuzzi et al., Lancet 337, pp. 750-752, 1991.

"Prevention of Autoimmune Diabetes in the BB Rat by Intrathymic Islet Transplantation at Birth," Posselt et al., Science vol. 256, pp. 1321-1324, May 1992.

"Thymus-Mediated Immune Tolerance to Renal Allograft is Donor but Not Tissue Specific,"Perico et al., J.Am.Sco. Nephrol vol. 2, No. 6, pp. 1063-1071, 1991.

"Regeneration of the thymus in old male rats treated with a stable analogue of LHRH," Greenstein et al., J.Endocrinol 112, pp. 345-350, 1987.

"Thyroid Function Modulates Thymic Endocrine Activity," Fabris et al., J.Clin. Endocrinal. Metab. vol. 62, No. 3, pp. 474-478, 1986.

"Zinc, Immunity, and Aging," Fabris et al., (A.L. Goldstein, Ed.), Plenum Press, New York, pp. 271-281, 1990.

"Coenzyme Q, the Immune System and Aging," Buznakov, Biomedical and Clinical Aspects of Coenzyme Q, vol. 3 (K. Folkers and Y. Yamamura, eds.), Elsevier/North Holland Biomedical Press, New York, pp. 311-323, 1981.

"Dehydroepiandrosterone Reduces Serum Low Density Lipoprotein Levels and Body Fat but Does not Alter Insulin Sensitivity in Norman Men," Nestler et al., J.Clin. Endrocrinol. Metab. vol. 66, No. 1, pp. 57-61, 1988.

"A Prospective Study of Dehydroepiandrosterone Sulfate, Mortality, and Cardiovascular Disease," Barrett-Conner et al., New England J. Med. vol. 315, No. 24, pp. 1519-1524, 1986.

"Role of Adrenal and Gonadal Androgens in Insulin Action and Metabolism," Kitabchi et al., Folia Endocrinol. 67, pp. 203-213, 1991.

"The influence of preoperative drug treatment on the extent of hyperplasia of the thymus in primary thyrotoxicosis," Simpson et al., Clin. exp. Immunol. 22, pp. 249-255, 1975.

"Short-Term and Long-Term Possibilities for Interventive Gerontology," Fahy, The Mount Sinai Journal of Medicine, vol. 58, No. 4, pp. 328-340, Sep. 1991.

"Reduction of Atherosclerosis by Administration of Dehydroepiandrosterone," Gordon et al., J.Clin.Invest., The American Society for Clinical Invest., Inc., vol. 82, pp. 712-720, Aug. 1988.

"Intrathymic Islet Transplantation in the Spontaneously Diabetic BB Rat," Ann. Surg. vol. 214, No. 4, 1991, Posselt et al., pp. 363-373.

"Immunological Tolerance to a Defined Myelin Basic Protein Antigen Administered Intrathymically," The Journal of Immunology, vol. 153, 1994, Goss et al., pp. 3890-3898.

"Intrathymic Implants of Genetically Modified Fibroblasts," The FASEB Journal, vol. 6, Jul. 1992, Behara et al., pp. 2853-2858.

"Prevention of Diabetes and Insulitis by Neonatal Intrathymic Islet Administration in NOD Mice," Journal of Autoimmunity Vol. 7, 1994, Charlton et al., pp. 549-560.

"Effect of Bovine Growth Hormone Administration on the Pattern of Thymic Involution in Mice," Thymus, vol. 23, 1994, Bar-Dayan et al., pp. 95-101.

"A Murine Model for Regeneration of the Senescent Thymus Using Growth Hormone Therapy," AGING: Immunology and Infection Disease, vol. 3, No. 1, 1991, McCormick et al., pp. 19-26.

"Protection From Glucocorticoid Induced Thymic Involution By Dehydroepiandrosterone," Pediatric Res, vol. 25 (4 pt 2), 1989, May et al., p 89A.

"The Role of the Thymus in Multiple Sclerosis," The Italian Journal of Neurological Sciences, vol. 10, 1989, D'Andrea et al., pp. 43-48.

Judd, MD, R. and Bueso-Ramos, MD, C., "Combined True Thymic Hyperplasia and Lymphoid Hyperplasia In Graves' Disease," *Pediatric Pathology*, vol. 10, pp. 829-836, 1990.

METHOD FOR THE PREVENTION OF TRANSPLANT REJECTION

CROSS REFERENCE TO RELATED APPLICATION

This application is a divisional of U.S. application Ser. No. 08/251,384, filed May 31, 1994, now U.S. Pat. No. 6,297,212.

BACKGROUND OF THE INVENTION

The present invention relates to human growth hormone therapy and to the cure of human disease through organ and tissue transplantation. The present invention includes a method for regenerating the human thymus to allow intrathymic transplantation and thereby the elimination of organ and tissue rejection. There are two variations of this method, one that employs growth hormone and one that employs agent that can substitute for growth hormone's thymus-regenerating effects. The former method has wide applicability beyond the transplantation of tissues and organs, because it involves the elimination of the most important side effects of growth hormone. Human growth hormone (HGH) has been recognized as a treatment for children of short stature or with renal failure, and has been a safe and effective treatment in most cases, but there are several reports that such children often experience hyperinsulinemia as a result of HGH administration. Further, HGH has been considered as a powerful approach to the treatment of human aging, but its widespread use is inhibited by its serious side effects, the most important of which is elevation of fasting and glucose-stimulated insulin levels, a phenomenon that is known to be a risk factor for atherosclerosis and cardiovascular disease. Arginine, an HGH releaser, has therapeutic effects in its own right, but has the same drawback of elevating blood insulin levels. The invention described here permits HGH therapy to be administered with no elevation in blood levels of insulin.

Much has been written of late about the growing excitement of anti-aging (gerolytic) therapies, including hormone replacement therapy with dehydroepiandrosterone (DHEA), melatonin, sex hormones, thyroid hormone, cortisol, or human growth hormone. Of these, the work of Rudman has attracted the most attention because of his statement that administration of human growth hormone (HGH) produced the same effects as the reversal of 20 years of aging. Rudman and others have, in fact, amassed an impressive body of evidence indicating that it is the loss of HGH with age that is responsible for much of the human aging process, including atrophy of internal body organs, thinning of the skin, slowing of cell division, weakening of muscles and bones, and accumulation of body fat. Even immune system decline with age seems largely dependent on loss of HGH. Furthermore, GH administration to animals produces a radical increase in longevity.

On the other hand, Marcus et al. have shown the down side of HGH: given at the minimum doses used in Marcus' study, equivalent to the doses used by Rudman, HGH produced dramatic and disturbing rises in fasting and stimulated serum insulin levels. The administration of HGH is known to decrease the body's sensitivity (i.e., responsiveness) to insulin, thus causing a compensating rise in pancreatic insulin output and therefore in serum insulin levels; yet paradoxically, falling HGH levels in aging humans are accompanied by increasing serum insulin levels.

Elevated insulin, in turn, has been linked in many studies and via many mechanisms to the development of atherosclerosis, hypertension, and heart disease. It is absolutely a major factor holding back the widespread clinical application of HGH for combatting many of the maladies of aging, dimming the attraction of this otherwise spectacular anti-aging intervention. HGH also leads to mild rises in serum cholesterol and triglycerides, raises blood pressure, and may produce symptoms similar to arthritis.

Of all the developments in modern immunology that promise to make the rejection of transplanted cells, tissues, and organs obsolete, the most exciting is the technique of intrathymic transplantation pioneered by Naji et al. This is so because the method requires no specific attention to the details of the rejection process, can be applied to the transplantation of virtually any tissue or organ into virtually any recipient, probably including even transplantation between unrelated species, without complex tailor-made immunopharmaceuticals, and with minimal trauma to the recipient, and can reverse established autoimmune disorders including autoimmune diabetes. The method involves first transplanting a biopsy sample of the graft into the thymus of the recipient and then transplanting the graft itself after a predetermined time. The presence of the intrathymic biopsy renders the host tolerant to the graft itself, either by eliminating or anergizing immune cells that attack the biopsy in the thymus. In addition, it is likely that, in the case of autoimmunity, the host can be made tolerant of its own tissue again by transplanting it into the thymus, thus reversing autoimmunity. Contrary to the presumption that tolerization will require a longer time than the ex vivo lifetime of the graft to be transplanted, recent studies have shown that success can be achieved when kidneys are transplanted into the recipient within 24 hours of the time the renal biopsy is placed into the recipient's thymus. Rejection is suppressed in the short run by a single dose of antilymphocyte globulin and/or by other conventional immunosuppression until tolerization makes further immunosuppression unnecessary. Bone marrow transplantation is also believed to induce tolerance to subsequent grafts from the same donor by the migration of bone marrow cells into the thymus, an equivalent process to transplantation of actual organ tissue samples in the thymus.

The main problem with this method is that it requires a functioning thymus gland of significant mass in order To be effective. The human thymus begins to involute before the age of 20 and becomes severely atrophied by the age of 40, and transplant surgeons and immunologists are at a loss for a way of overcoming this problem. In fact, it is thought that age-related thymic involution accounts for a major part of age-related morbidity and mortality and therefore represents a major unsolved health problem worthy of solution in its own right.

What has not been recognized by the medical community is that thymic regeneration is possible in humans. Many animal studies attest to the feasibility of thymic regeneration in animals using several different methods. Several human studies have shown that immune system function can be restored in older humans, but it has never been suggested that this is due to thymic regeneration. The present invention effects thymic regeneration in man.

Several methods have been shown capable of reversing thymic involution in animals and, by inference, in man, but none are feasible for human use. Administering a male contraceptive to rats results in dramatic thymic regeneration, but would not be desirable in humans for a variety of reasons, including major testicular shrinkage. It has been recognized that hyperthyroid humans do not undergo age-related thymic involution, and that administration of thyroid hormone to older humans results in a restoration of youthful indices of immune system function, but administration of thyroid hormone is considered hazardous, and hyperthyroid individuals have a number of medical problems. The problems of regenerating the thymus of diabetic animals or humans have not been considered at all in the prior art.

As noted above, the use of growth hormone alone for this purpose would be contraindicated by the adverse effect of growth hormone on insulin sensitivity, despite the ability of growth hormone to regenerate the thymus in rodents and dogs and to improve immunity in older humans. Growth hormone use for thymic regeneration could lead to unacceptable loss of control of insulin responsiveness in diabetics and elevated insulin levels in nondiabetics. In fact, since elevated insulin leads to virtually all of the side effects of growth hormone (hypertension, atherosclerosis, water retention, and cardiovascular morbidity), it is possible that most of these side effects are a result, at least in part, of the elevation of insulin produced by growth hormone.

SUMMARY OF THE INVENTION

In the present invention, it has been surprisingly discovered that one can increase a patient's level of human growth hormone without causing a corresponding increase in serum insulin levels by administering either human growth hormone (HGH) or its equivalent (active HGH analog, HGH metabolite or fragment, HGH mimic, HGH releaser or mixtures thereof) in combination with dehydroepiandrosterone (DHEA) or its equivalent (DHEA-sulfate, other DHEA precursor, DHEA releaser, DHEA metabolite(s), DHEA equivalent analog, or mixtures thereof). (Here we define a "mimic" as a structurally dissimilar compound that has the same biologic action as the natural biological molecule.) This is surprising, in that human data militate against an insulin-suppressing effect of DHEA in normal people, and suggest that DHEA administration can actually elevate insulin levels indirectly.

In another aspect of the invention, it has been surprisingly determined that in addition to effecting other positive results associated with human growth hormone treatment, the above regimen can permit the cure of diabetes and a range of other diseases by actually regenerating the human thymus and thereby allowing subsequent intrathymic transplantation.

These and other objects, advantages and features of the present invention will be more fully understood and appreciated by reference to the appended specification and drawings.

DESCRIPTION OF THE PREFERRED EMBODIMENTS

General Procedure

In the preferred embodiment, human growth hormone (HGH) or its equivalent analog, metabolite, fragment, releaser, mimic, or mixture thereof is administered by subcutaneous injection or other efficacious route every day or every other day or three times a week (e.g., Monday, Wednesday and Friday) at an HGH equivalent dose of 0.01 to 0.05 mg/kg of body weight, the dose being adjusted to avoid peak levels of growth hormone or somatomedin C greater than those found in individuals that are 10–30 years of age. (Peak levels similar to those 10–20 years of age are appropriate for thymic regeneration; levels similar to those of 20–30 year olds are appropriate for chronic growth hormone replacement therapy.)

The most desirable target range for somatomedin C levels in men and women for long-term growth hormone replacement therapy is 700–3000 units/L, and particularly 1000–1600 units/L (where 1 unit equals 150 ng of somatomedin C). For short-term thymus regeneration, the target somatomedin C levels are 700–7000 (most preferably 700–5000) units/L for women and 700–6000 (most preferably 700–3000) units/L for men. Simultaneously with or slightly before HGH administration, DHEA, DHEA precursor (such as DHEA-S), DHEA releaser, equivalent metabolite, equivalent DHEA analog or a mixture thereof is given orally or via another efficacious route at a DHEA equivalent dose of 50–2000 mg, more preferably 50–1000 mg/day, the dose being adjusted based on the circulating DHEA level (not to exceed levels found in individuals 20–25 years of age by more than 100%) and the response of circulating insulin levels (insulin levels should be adjusted by DHEA dose until they are at or below the pre-HGH insulin basal levels). The most desirable target range for circulating DHEA is 300–800 ng/dl. This regimen should be continued preferably for 1–3 months before intrathymic transplantation, and/or indefinitely for applications related to aging or growth.

The term HGH is intended to include recombinant or natural human growth hormone. HGH releasers are compounds which stimulate the body's production and/or release of HGH and include, but are not limited to, growth hormone releasing hormone (GHRH), clonidine, phenylalanine, L-DOPA, arginine, ornithine, deprenyl, and somatostatin inhibitors. HGH will be effective whether it is supplied exogenously or released from the pituitary by such releasing agents. Consequently, the use of a growth hormone releaser is an acceptable variation on the use of growth hormone itself, in those patients who are able to release adequate growth hormone in response to such agents. Patients who are able to release appreciable but not sufficient HGH in response to such agents may be given both a releasing agent and exogenous HGH so as to attain the required HGH levels for thymic regeneration while minimizing the use of exogenous HGH, which is expected to be more expensive than HGH releasers. Furthermore, the entire HGH molecule may not be required for HGH action. Therefore, equivalent analogs such as genetically-engineered variants or fragments of HGH that retain the biological activity of HGH but that are less expensive or have fewer side effects are also acceptable variations. The dosage for any of these HGH alternatives are "HGH equivalent doses," that is they should yield the same desired level of or effect of HGH in the body. An example of an HGH "mimic" would be somatomedin C. The best mode process is also compatible with administration of drugs that block other side affects of HIGH, e.g., parlodel to block gynecomastia in men.

DHEA should be given "to effect." "To effect" is defined as sufficient to lower that particular patient's insulin levels down to either basal levels or, if basal levels are elevated in comparison to an accepted standard for good health and long life, to levels deemed to maximize longevity and health. Typically, this will involve most preferably DHEA doses of 50–1000 mg/day, a range considerably below the "overkill" doses of 1600 to 2500 mg/day being employed routinely in human clinical trials, which maximize the danger of complications such as masculinization of women or worsening of benign prostatic hypertrophy in men. All routes of administration fall within the limits of the best mode process, and the substitution of any DHEA precursor, releaser (such as an enzyme that cleaves DHEA-S to "release" DHEA), equivalent DHEA metabolite or equivalent analog of DHEA that has the same insulin-suppressing role as DHEA itself constitutes an acceptable variation, including combinations of DHEA and agents that block any undesired effects of DHEA.

DHEA-sulfate is an example of a DHEA precursor. Although DHEA is considered to be active and DHEA-sulfate to be inactive, tissue enzymes exist that convert DHEA-sulfate into DHEA in the body. Consequently, DHEA-sulfate rather than DHEA itself may be administered in a dose appropriate to raise DHEA levels to insulin-suppressing values (or to produce similar insulin suppression directly). The term DHEA releaser is intended to include any other compound which causes the body to produce or release DHEA in the body. The dosage required for any of the alternatives to DHEA per se should be "DHEA equivalent doses," that is, doses that yield the same insulin lowering effect as the indicated doses of DHEA.

The precise mechanism of operation of the preferred embodiment is not known. DHEA does not simply eliminate excess insulin, and indeed that would be undesirable, since the increased insulin level is in response to the body's reduced insulin sensitivity. Rather, DHEA apparently directly counters the desensitizing effects of HGH, thus allowing the body to obtain the same glucose uptake with lower, indeed normal, insulin levels.

Adding DHEA to counter the insulin-raising effects of growth hormone is compatible with the use of any drugs that may be developed that limit the conversion of DHEA to masculinizing androgens in either women or men or otherwise suppress DHEA or DHEA-sulfate side effects. The optimum dose of DHEA is that dose that successfully suppresses insulin to the desired level and maximizes subsidiary benefits such as inhibition of atherosclerosis without producing side effects.

The time of DHEA administration is optimally close to the time of administration of HIGH so that DHEA will be present in the blood stream when the insulin-elevating tendency of HGH is maximal. For example, oral arginine taken just before bedtime should be accompanied by DHEA. A pharmaceutical agent consisting of HGH+DHEA or HGH releaser+DHEA or HGH analog+DHEA or any of these HGH variants+DHEA analogs or DHEA-sulfate, etc., would embody this best mode approach. However, the process of using DHEA to suppress insulin includes administration at other times as well. The effects of HGH on human physiology last approximately six months or more. Consequently, administration of DHEA or its equivalent to suppress insulin elevated by previous HGH administration or its equivalent is valid at any time insulin is elevated by prior HGH or HGH equivalent administration.

Experimental Results

Experiment 1: Administration of Arginine (An HGH Releaser) and DHEA

A human patient was placed on a standardized regimen of nutrient intake for two weeks to establish a baseline prior to ingesting any HGH releasing agents. The evening prior to blood analysis, the same evening meal was consumed (salmon, potato, white wine, vegetables, and Caesar salad). Upon establishing basal values for glucose, insulin, somatomedin C (a marker for growth hormone), DHEA-sulfate, serum lipids, and testosterone, a daily regimen of ingesting 15 grams of arginine just before bedtime was instituted. This regimen was maintained for one week, after which a new baseline was obtained. The evening following this new baseline measurement, DHEA was ingested at a dose of 180 mg (two 90 mg capsules taken simultaneously) at the same time as the arginine. This was continued for one week and the baseline levels of metabolites were rechecked. Finally, for the last week, the arginine dose was administered every other day or at 7.5 g/day while DHEA levels were maintained. Thus, the data points are as follows:

1: Baseline—begin 15 gm/day administration of arginine;
2: Day 7—begin 180 mg/day DHEA;
3: Day 14—begin 15 gm arginine every other day or 7.5 g/day; and
4: Day 21—end of experiment, no arginine administered the previous night.

Figure 1:
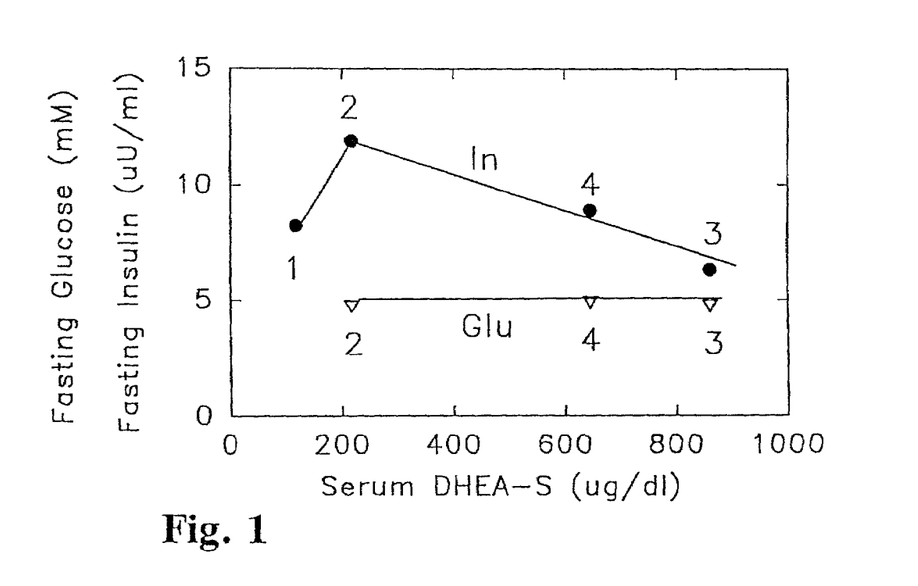
FIG. 1 charts serum fasting glucose and fasting insulin levels against serum DHEA-sulfate levels in an arginine (HGH releaser) administration experiment involving DHEA administration.
Figure 2:
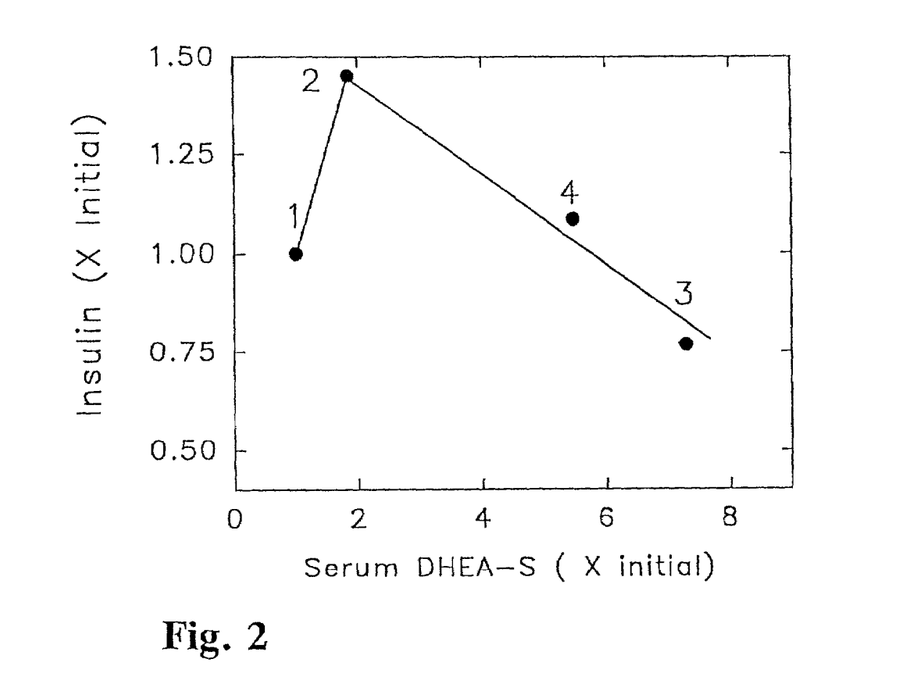
FIG. 2 charts the relative change in insulin level against the relative change in serum DHEA-sulfate level in the same experiment as FIG. 1.

The primary results are given in FIG. 1 and FIG. 2, which document the changes in insulin and glucose levels that accompanied the introduction and tapering off of arginine administration and their relationship to DHEA (reflected in FIG. 1 by DHEA-sulfate due to a missing basal value for DHEA itself). There was no change in glucose concentration, which is consistent with the known lack of effect of HGH on glucose concentrations. On the other hand, fasting serum insulin rose nearly 50% in response to arginine ingestion (point 2), but was brought down to only 76% of basal levels by the ingestion of DHEA, despite the continuing and undiminished administration of arginine (point 3). This data point thus provides the crucial validation of the hypothesis and the key to removing the side effects of HGH administration. Point 4 gives the result of dropping arginine administration to a regimen of every other day ingestion, no ingestion having taken place the night prior to the blood analysis represented. Here insulin has returned to basal levels. The significance of this point is that it shows the combination of HGH release and DHEA administration regimens that precisely balances the effects of these two hormones on insulin levels.

There are two other aspects of FIGS. 1 and 2 that seem significant. First, accompanying the elevation of insulin that results from arginine ingestion (point 2 versus point 1) is a noticeable increase in DHEA-sulfate. This is an endogenous increase, since no DHEA was ingested over this period, and establishes a putative link between the release of HGH and DHEA. This link is confirmed by comparing points 3 and 4, which show that, with no drop in DHEA ingestion, the circulating level of DHEA-sulfate fell in response to the fall in arginine ingestion. From these results, it would appear that DHEA levels are normally modulated by growth hormone so as to buffer the effects of growth hormone on insulin. This is consistent with animal studies showing a DHEA-releasing effect of growth hormone. With aging, DHEA levels become insufficient to carry out this function, since DHEA falls faster with age than does HGH, and a rise in insulin is thus expected.

Figure 3:
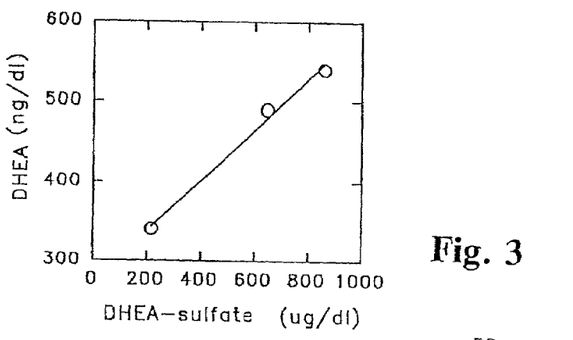
FIG. 3 graphs DHEA serum concentration against serum concentration for DHEA-sulfate.

FIG. 3 shows the correlation between DHEA-sulfate and DHEA in this study. The correlation appears adequate to use in assuming that the DHEA-sulfate levels shown in FIG. 1 reflect DHEA levels.

Figure 4:
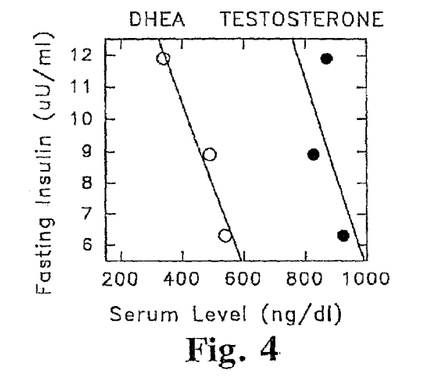
FIG. 4 compares the correlation between insulin level and either DHEA concentration or testosterone concentration.

FIG. 4 presents evidence that the effect of DHEA is due to DHEA itself rather than testosterone, which rises upon DHEA administration and has been linked to insulin sensitivity in women with polycystic ovarian syndrome. FIG. 4 shows that the correlation between insulin and DHEA is far better than the correlation between insulin and testosterone, contrary to previous results with these women. (Lines are least squares regression fits.)

Figure 5:
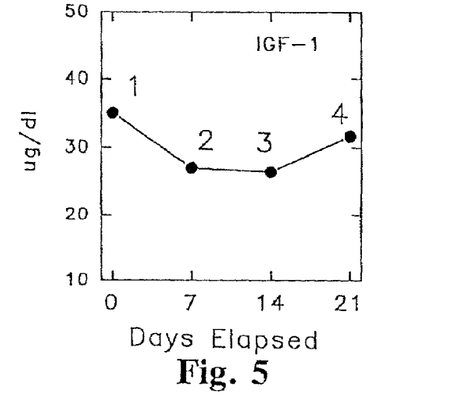
FIG. 5 charts the blood serum level of IGF-1 against time in an arginine and DHEA administration experiment.

FIG. 5 shows a paradoxical result, namely, an actual DROP, as opposed to the expected RISE, in somatomedin C (also known as IGF-1) levels in response to oral arginine. This drop was sustained as long as arginine administration was continued. An independent experiment confirmed this IGF-1lowering effect of arginine: basal levels of 223 ng/ml fell to 166 ng/ml two hours after arginine ingestion. Direct addition of arginine to the serum sample to determine whether arginine interferes with the chemical assay for IGF-1 indicated that 4 mM arginine made IGF-1 levels read higher than 1 mM arginine in the serum, not lower, arguing that the IGF-1-lowering effect is real, not artifactual. Others have also measured somatomedin C levels following arginine ingestion or infusion, and found them to be depressed despite good release of HGH. There is no explanation for this paradox, but it is not material to the fact that HGH is released by arginine and that released HGH does elevate insulin and that DHEA does block this insulin-elevating effect.

Arginine is known to be a secretagogue for insulin in its own right, and the possibility that it could be responsible for a major part of the insulin elevation observed must be considered. However, this possibility appears unlikely for the following reasons. First, the time course of insulin elevation in humans following arginine ingestion or infusion is rapid: insulin levels peak in about 30 minutes or less and fall back to baseline within 1–2 hours, whereas in the experiment reported in FIG. 1, insulin was measured 11–13 hours after arginine ingestion. Insulin at that late tune could only have been affected by long-term secondary effects of arginine ingestion, i.e., HGH release and its resulting insulin elevation, which takes more than 6 hours to fully develop. Further, in the experiment described in FIG. 1, an insulin determination after only 3 days of arginine ingestion revealed a normal insulin level (data not shown in FIG. 1), indicating that it is not the acute and direct insulin-releasing effect of arginine that is primarily responsible for the insulin elevation observed, but insulin resistance derived from delayed arginine-induced HGH release.

Experiment 2: Administration of HGH and DHEA

The above-described experiment is based on the generally accepted assumption and observation that arginine activates the endogenous release of HGH. This second experiment was conducted to confirm comparable results from the direct administration of HGH.

As in the first experiment, a standard dietary regimen was followed the evening before each blood sample was collected. HGH administration was initiated one day after a baseline blood sample was drawn. HGH was injected subcutaneously at a dose of approximately 0.018 mg/kg/day, every other night, and was injected near midnight prior to blood collection the following morning. Blood was collected between 10:30 and 11:00 a.m. The second blood sample was taken on day 8, or just over 7 days after beginning HGH injections (4 injections in total to that time). After this second blood sample, a "wash out" period of two days was allowed prior to reinitiating injections according to the same schedule. On day 9, during the HGH "wash out" period, a priming dose of 200 mg of DHEA was taken in divided doses to prepare the patient for the HGH. The second round of injections was done simultaneously with the ingestion of two 100 mg capsules of DHEA, beginning on the evening of day 10. This regimen continued for a total of 4 HGH injections, culminating in the final injection on day 16 and blood sampling on day 17. Two hundred mg of DHEA were taken also on the nights between HGH injections, at the normal time. HGH injections were administered near midnight of the day stated.

Figure 6:
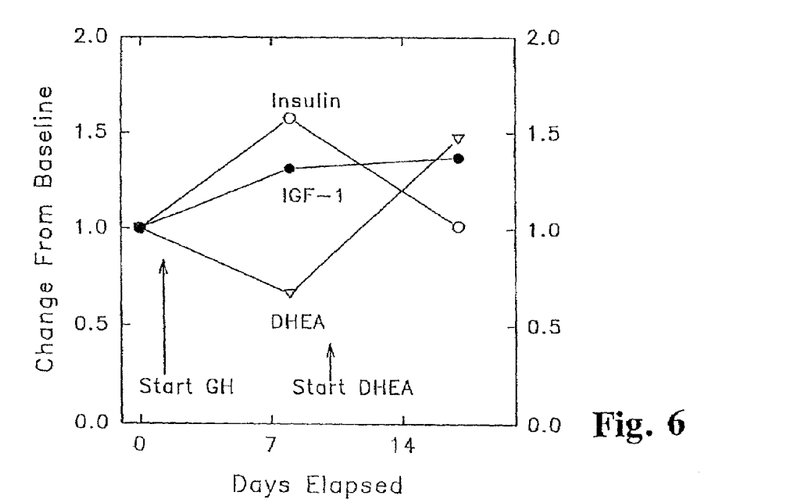
FIG. 6 charts serum insulin, IGF-1 and DHEA against time, during a protocol involving administration of HGH and DHEA.

The results of this experiment are shown in FIG. 6 and Table 1. The effects on insulin are virtually identical to those of the original arginine experiment, insulin rising by 57% prior to DHEA ingestion and falling to 101.5% of control levels after combining HGH with DHEA. Therefore, there is no doubt of the antihyperinsulinemic effect of DHEA in the presence of hyperinsulinemia inducing doses of HGH, a phenomenon that has never before been documented or suspected. Further, there is no doubt that currently recommended doses of HGH do produce a serious hyperinsulinemia effect. HGH actually depressed circulating DHEA levels by a third while leaving DHEA-sulfate unaltered; this is presumably a manifestation of the well-known DHEA-depressing effect of insulin, and is different from the net DHEA-sulfate-elevating effect, and apparent DHEA-elevating effect, of arginine administration documented above. This may reflect the depressed IGF-1 levels in the arginine protocol versus the elevated IGF-1 levels with HGH administration, and is explicable if IGF-1 ("insulin-like" growth factor) contributes to the suppression of DHEA by a mechanism similar to that of insulin. Regardless, the large change in DHEA level farther supports functional interrelationships between HGH and DHEA. In fact, it is fascinating that DHEA appears to govern the differential effects of HGH on IGF-1 versus insulin, allowing IGF-1 to rise with HGH administration (desirable) while insulin remains unchanged (desirable) despite the similarities of the two. The exact data for all metabolites measured are reported in Table 1.

TABLE 1

| | | Level | | |
|---|---|---|---|---|
| Metabolite | Stage of Experiment: | Baseline | HGH only | HGH + DHEA |
| Insulin (uU/ml) | | 6.6 | 10.4 | 6.7 |
| IGF-1 (ug/dl) | | 27.0 | 35.5 | 37.1 |
| DHEA (ng/dl) | | 360 | 240 | 530 |
| DHEA-sulfate (ug/dl) | | 146 | 146 | 688 |

Direct Applications of DHEA and HGH Coadministration

Some obvious implications of the successful reversal of the most troubling side effect of HGH administration, the rise in serum insulin and the fall in insulin sensitivity, are (a) the ability to use HGH in many more normal individuals for the direct treatment of aging with minimal fear of side effects, (b) the ability to use HGH in older diabetics, whose need for HGH probably exceeds that of normal elderly individuals but whose ability to take HGH would be ruled out by most physicians in the absence of a means of normalizing insulin sensitivity, and (c) the ability to use HGH to treat younger people suffering from both pituitary insufficiency and adrenal insufficiency. The combination of DHEA and arginine may also be useful when arginine is used in doses below the HGH-releasing dose to stimulate immunity or when arginine is used as a laxative or for other purposes. The applications mentioned also pertain to the physiological equivalents of HGH+DHEA.

Curing Diabetes With HGH and DHEA Coadministration

A nonobvious application is to cure diseases such as diabetes. The key to this application is the ability to use DHEA+HGH to regenerate the human thymus. Most age-related immune system decline is caused by thymic involution (atrophy). Thymic involution is not now a clinically treatable condition, and it affects virtually 100% of the adult population. The concurrent administration of human growth hormone or an HGH releaser and DHEA, its metabolites or equivalent analogs surprisingly reverses thymic involution in older individuals and in others with thymic insufficiency.

By regenerating the previously atrophied thymus, this coadministration of HIGH and DHEA allows intrathymic transplantation in elderly or involuted individuals as a route to permanent grafting of tissues and organs without immunosuppression and without rejection, a technique not formerly applicable to those over the age of 30–40 or to those patients with atrophied thymuses (e.g., hypothyroid patients). Three immediate applications of this method are the cure of insulin dependent diabetes, the reversal of autoimmune conditions in those over 30, and the engrafting of older individuals with organs or with genetically engineered cells and tissues from unrelated sources without rejection and without chronic immunosuppression.

The regimen for administering human growth hormone and DHEA or their equivalents for the rejuvenation of the thymus is as described above in the preferred embodiment. The regimen should be continued preferably for 1–3 months. For best results, this regimen can be supplemented with other immune-system strengthening agents, particularly coenzyme $Q_{10}$ (10–200 mg/day), Vitamin E (200–1000 IU/day) and zinc (30–100 mg/day). Further, chromium picolinate (100–1000 micrograms/day) may be used to supplement DHEA/DHEA-sulfate.

After thymic regeneration, the thymus should be imaged (preferably by magnetic resonance imaging, though other methods are also acceptable) to verify regeneration and thymic location. Surgery should then take place on the same day as or the day after HGH and DHEA are administered according to the protocol specified above. At this time, a surgeon skilled at thymic biopsy retrieval injects into the thymus an appropriate sample of the tissue or organ to be transplanted later, or injects any other donor-specific cells or antigens (for example, bone marrow cells) that are the immunological equivalent of the tissue itself in stimulating deletion or anergy of the cells otherwise responsible for later rejecting the transplanted tissue or organ. This tissue may be an endogenously-derived sample in the case of those with autoimmune diseases, e.g., myelin from the cauda equina to reverse multiple sclerosis; a joint biopsy to reverse autoimmune arthritis; or endogenous islets to reverse incipient diabetes in the case of diabetes that has not progressed to the point of major islet die-off. The amount of injected tissue is equivalent to $\frac{1}{10}$th to twice the amount specified by Naji's prior art for animals without thymic atrophy (based on the ratio of thymic volume to volume of the injected tissue and/or on the ratio of the volume of injected tissue to body weight). A variation on direct intrathymic injection is peripheral injection of cells that spontaneously migrate to the regenerated thymus (e.g., bone marrow cells) and thus induce tolerance.

At the same time the intrathymic or peripheral injection is given, the patient is given a standard dose of antilymphocyte globulin or other appropriate immunosuppressant to ensure persistence of the intrathymic graft until the recipient's immune system becomes tolerant of the donor's tissues. The desired tissue or organ transplant itself may be given on the same day as the intrathymic injection, accompanied by maintenance immunosuppression until tolerance is attained, or this transplantation may be delayed until tolerance is attained, in order to avoid the need for immunosuppression lasting longer than 1–2 weeks, or to avoid the need for higher doses of immunosuppressants.

In the case of curing diabetes, it is desirable to inject pancreatic islets into the thymus in order to be able to judge the "take" of injected material based on islet function and in order to attain some preliminary minimal protection from diabetes prior to the subsequent transplantation of islets by infusion into the portal vein or other site.

In the case of reversing autoimmunity, the priming injection to the thymus need not be followed by further transplants unless an additional intrathymic endogenous tissue sample is required to facilitate reversal of the autoimmune state. For such patients, anti-rejection medication should be used sparingly or not at all.

Alternative Embodiments for Thymic Regeneration

In broader aspects of thymic regeneration to facilitate thymic injection and subsequent organ and tissue transplantation, alternative methods for regenerating the thymus can be utilized. First, insulin sensitizing (and therefore lowering) agents other than DHEA and its above-described relatives can be employed in place of DHEA. Chromium picolinate and similar formulae involving chromium (such as "GTF" or glucose tolerance factor preparations available in health food stores) and phenformin represent the only known members of this class of agents. As in the case of DHEA, the appropriate dose is to be adjusted based on the insulin-lowering response attained in a particular patient. Chromium picolinate is particularly exciting because of its low toxicity, its ability to extend the life span of animals by 50%, and because its ability to increase insulin sensitivity is a key anti-aging effect. The action of chromium picolinate is not considered to be similar to the actions of DHEA in humans in the prior art because the insulin-lowering effect of DHEA is unknown in the prior art. Although the ability of chromium picolinate to reverse GH-induced elevation of insulin levels has been reported in passing in pigs, its use in regenerating the thymus has never been contemplated in the prior art, the further application of this regeneration to tissue and organ transplantation has similarly never been previously contemplated, and its use in combination with HGH for these ends has also not been contemplated in the prior art.

A last approach to regenerating the thymus is to use agents other than the equivalent of HGH and DHEA, whose thymus-regenerating effect substitutes for that of growth hormone but does not involve elevation of insulin levels. In particular, the use of zinc alone, Vitamin E alone, or coenzyme $Q_{10}$ alone have shown promise in restoring immune system function in elderly animals and humans. The use of all three agents together provides an improved method of stimulating immunity that will regenerate the thymus sufficiently to permit subsequent intrathymic transplants without producing undesirable effects on insulin sensitivity. Consequently, a third choice for thymic regeneration is to use 30–130 mg/day of zinc plus 200–1000 IU/day of Vitamin E plus 10–200 mg/day of coenzyme $Q_{10}$ for 1–3 months. This approach will be desirable when HGH and DHEA or their equivalents cannot be used for any reason.

Of course, it is understood that the foregoing are merely preferred embodiments of the invention and that various changes and alterations can be made without depart from the spirit and broader aspects thereof, as set forth in the appended claims.

The invention claimed is:

1. A method for transplanting organs and grafting tissue into a patient comprising steps of:
   restoring immune system function by regenerating the patient's involuted thymus;
   injecting the immunological equivalent of the tissue or organ to be transplanted into the patient, into the regenerated thymus (or, in the case of bone marrow cells, peripherally); and
   then transplanting said organ or grafting said tissue.

2. The method of claim 1, in which the step of injecting is achieved by an intrathymic injection in which said patient is given a dose of immunosuppressant at approximately the same time the intrathymic injection is administered.

3. The method of claim 2, in which the desired tissue or organ transplant is performed on the same day as the intrathymic injection, accompanied by maintenance of immunosuppression until tolerance is achieved.

4. The method of claim 2, in which transplantation of the desired organ or tissue is delayed until organ or tissue tolerance has been achieved.

5. The method of claim 1, in which said step of restoring immune system function by regenerating said patient's thymus is performed by administering a first compound consisting of one of human growth hormone, human growth hormone analogs, human growth hormone precursors, human growth hormone metabolites, human growth hormone releasers, human growth hormone mimics, and mixtures thereof in combination with a second compound consisting of one of DHEA, DHEA precursors, DHEA releasers, DHEA analogs, DHEA metabolites and combinations thereof.

6. The method of claim 1 in which said step of restoring immune system function by regenerating said patient's thymus is performed by: administering a first compound selected from the group consisting of human growth hormone, human growth hormone analogs, human growth hormone precursors, human growth hormone metabolites and human growth hormone releasers or mimics and mixtures thereof, combined with the approximately simultaneous administration of a second compound selected from the group consisting of chromium picolinate and equivalent chromium containing compounds and phenformin.

7. The method of claim 1, in which said step of restoring immune system function by regenerating said patient's thymus includes: administering zinc, Vitamin E and coenzyme $Q_{10}$.

8. The method of claim 7 in which said zinc is administered at 30–130 mg/60 kg body weight per day; Vitamin E is administered at 200–1000 IU/day/60 kg of body weight; and coenzyme $Q_{10}$ is administered at 10–200 mg/day.

9. The method of claim 1, wherein the immunological equivalent of the tissue or organs to be transplanted into the patient is endogenous material.

10. The method of claim 1, wherein the immunological equivalent of the tissue or organs to be transplanted into the patient is exogenous material.

* * * * *

UNITED STATES PATENT AND TRADEMARK OFFICE
CERTIFICATE OF CORRECTION

| | | |
|---|---|---|
| PATENT NO. | : 7,166,569 B2 | Page 1 of 1 |
| APPLICATION NO. | : 09/933309 | |
| DATED | : January 23, 2007 | |
| INVENTOR(S) | : Gregory M. Fahy | |

It is certified that error appears in the above-identified patent and that said Letters Patent is hereby corrected as shown below:

Column 2:
Line 10, "modem" should be --modern--.
Line 45, "To" should be --to--.

Column 5:
Line 57, "HIGH" should be --HGH--.

Column 8:
Line 42, "farther" should be --further--.

Signed and Sealed this

Nineteenth Day of June, 2007

JON W. DUDAS
*Director of the United States Patent and Trademark Office*